United States Patent [19]

Förster et al.

[11] Patent Number: 4,509,971
[45] Date of Patent: Apr. 9, 1985

[54] BENZOTHIAZOLE SUBSTITUTED CARBOXYLIC ACID AMIDE COMPOUNDS AND HERBICIDAL METHODS COMPOSITIONS THEREOF

[75] Inventors: Heinz Förster; Wolfgang Hofer; Volker Mues, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 524,698

[22] Filed: Aug. 19, 1983

Related U.S. Application Data

[63] Continuation of Ser. No. 270,039, Jun. 3, 1981, abandoned, which is a continuation of Ser. No. 35,361, May 2, 1979, abandoned.

[30] Foreign Application Priority Data

May 20, 1978 [DE] Fed. Rep. of Germany ....... 2822155
Feb. 2, 1979 [DE] Fed. Rep. of Germany ....... 2903966

[51] Int. Cl.³ .................. A01N 43/78; A01N 43/90; C07D 417/12; C07D 277/68
[52] U.S. Cl. ...................... 71/90; 548/165; 548/151; 546/186; 260/245.5; 71/88; 71/92; 71/94
[58] Field of Search ............ 548/165; 71/90; 546/186; 260/245.5

[56] References Cited

U.S. PATENT DOCUMENTS 4,119,433 10/1978 Baker et al. .................... 71/118
4,130,413 12/1978 Handte et al. .................... 71/90

Primary Examiner—Glennon H. Hollrah
Assistant Examiner—D. B. Springer
Attorney, Agent, or Firm—Felfe & Lynch

[57] ABSTRACT

Novel substituted carboxylic acid amide compound of the formula

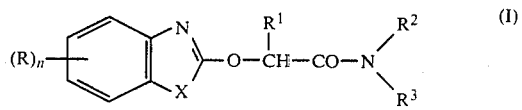

wherein
n is an integer from 1 to 4
each R is independently selected from hydrogen, halogen, alkyl, haloalkyl, alkoxy, haloalkoxy, alkylthio, haloalkylthio, amino, alkylamino, dialkylamino, nitro, cyano and alkoxycarbonyl; and two R radicals taken together can represent methylenedioxy, dichloromethylenedioxy or difluoromethylenedioxy,
$R^1$ is hydrogen or alkyl,
$R^2$ and $R^3$ are individually selected from hydrogen or a radical selected from alkyl, alkenyl, alkynyl, aralkyl, cycloalkyl, aryl and nitrogen-containing heterocycles, each of which radicals may be substituted and each of which radicals may, together with the nitrogen atom to which they are attached, form an optionally substituted, optionally partially unsaturated and optionally benzofused monocyclic or bicyclic radical, which may contain one or more further hetero-atoms, and X is oxygen or sulfur.

27 Claims, No Drawings

BENZOTHIAZOLE SUBSTITUTED CARBOXYLIC ACID AMIDE COMPOUNDS AND HERBICIDAL METHODS COMPOSITIONS THEREOF

This application is a continuation of application Ser. No. 270,039, filed June 3, 1981, which in turn is a continuation of Ser. No. 035,361, filed May 2, 1979, both abandoned.

The invention relates to certain new substituted carboxylic acid amide compounds, to herbicidal compositions containing such compounds and to methods of combating undesired vegetation utilizing such compounds.

It is already known that certain thiocarbamic acid esters, for example hexahydro-1-H-azepine-1-carbamic acid ethyl thioester (molinate) and N,N-diethyl-thiocarbamic acid S-(4-chlorobenzyl) ester (benthiocarb), have herbicidal properties (see U.S. Pat. No. 3,198,786 and DE-AS (German Auslegeschrift) No. 1,817,662). It is also known that certain phenoxyalkanecarboxylic acids and derivatives thereof, for example 2,4-dichlorophenoxyacetic acid (2,4-D) and 2,4-dichlorophenoxypropionic acid (2,4-DP), can be used as herbicides, in particular as growth factor herbicides (see, for example, H. Martin, Die wissenschaftlichen Grundlagen des Pflanzenschutzes (The Scientific Principles of Plant Protection), Verlag Chemie (1967) page 426 et seq.). However, the action of these commercially available products is now always completely satisfactory.

The present invention now provides, as new compounds, the substituted carboxylic acid amides of the general formula

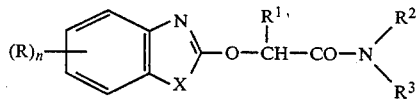

in which
n represents 1, 2, 3 or 4,
each R, individually and independently of any other, represents hydrogen, halogen, alkyl, halogenoalkyl, alkoxy, halogenoalkoxy, alkylthio, halogenoalkylthio, amino, alkylamino, dialkylamino, nitro, cyano, or alkoxycarbonyl, it also being possible for two radicals R together to represent the methylenedioxy, dichloromethylenedioxy or difluoromethylenedioxy group,
$R^1$ represents hydrogen or alkyl,
$R^2$ and $R^3$ are identical or different and individually represent hydrogen or an alkyl, alkenyl, alkynyl, aralkyl, cycloalkyl, aryl or nitrogen-containing heterocyclic radical, which in each case may be optionally substituted, or, together with the nitrogen atom to which they are bonded, form an optionally substituted, optionally partially unsaturated and optionally benzo-fused monocyclic or bicyclic radical, which optionally contains one or more further hetero-atoms, and
X represents oxygen or sulphur.

The substituted carboxylic acid amides (I) are distinguished by a powerful herbicidal activity.

Preferably, n represents 1, 2, 3 or 4,
each R individually represents hydrogen, chlorine, alkyl with 1 to 6 (especially 1 to 4) carbon atoms, trifluoromethyl, alkoxy or alkylthio with in either case 1 to 6 (especially 1 to 4) carbon atoms, trifluoromethoxy, trifluoromethylthio, nitro or cyano, or
two radicals R together represent the methylenedioxy, dichloromethylenedioxy or difluoromethylenedioxy group,
$R^1$ represents hydrogen or methyl,
$R^2$ and $R^3$, which can be identical or different, each represent hydrogen, straight-chain or branched alkyl with 1 to 20 carbon atoms, cyanoalkyl with 2 to 5 carbon atoms, alkoxyalkyl with 2 to 8 carbon atoms, alkylthioalkyl with 2 to 8 carbon atoms, alkenyl with 3 to 10 carbon atoms, alkynyl with 3 to 10 carbon atom, cycloalkyl with 3 to 12 carbon atoms, aralkyl with 1 to 2 carbon atoms in the alkyl part and 6 or 10 carbon atoms in the aryl part, aryl with 6 or 10 carbon atoms [it being possible for the two last-mentioned radicals to carry one or more substituents selected from 1 to 3 halogen atoms (especially fluorine, chlorine and/or bromine), 1 to 3 alkyl radicals with in each case 1 to 4 carbon atoms, nitro and cyano], morpholinyl or tetrahydrofurfuryl, or
$R^2$ and $R^3$, together with the nitrogen atom to which they are bonded, form an optionally partially unsaturated and/or optionally benzo-fused monocyclic or bicyclic radical with 3 to 15 carbon atoms, which is optionally substituted by 1 to 3 alkyl groups with in each case 1 to 5 carbon atoms (spiro-linked substituents with up to 4 carbon atoms and up to 2 oxygen atoms also being possible), or form a monocyclic radical, with in each case 3 to 10 carbon atoms, which is optionally substituted, saturated and contains a further nitrogen atom, an oxygen atom or a sulphur atom, and
X represents oxygen or sulphur.

The invention also provides a process for the preparation of a substituted carboxylic acid amide of the formula (I) in which an α-hydroxy-carboxylic acid amide of the general formula

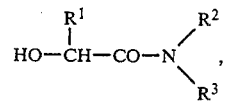

wherein
$R^1$, $R^2$ and $R^3$ have the meanings stated above, is reacted with a 2-halogeno-benzazole of the general formula

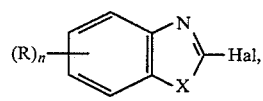

wherein
R, n and X have the meanings stated above and
Hal represents chlorine, fluorine, bromine or iodine, if appropriate in the presence of an acid acceptor and if appropriate in the presence of a diluent.

Surprisingly, the substituted carboxylic acid amides according to the invention exhibit a considerably better herbicidal action than the compounds of analogous structure and the same type of action which are known from the state of the art. It is particularly surprising that the active compounds according to the invention have an outstanding action against gramineae, while the structurally similar phenoxy-alkanecarboxylic acid derivatives, such as, for example, 2,4-D, display virtually no action against gramineae.

Those compounds of the formula (I) are particularly preferred in which n and R have the meanings given above as preferred, and in which R¹ represents hydrogen, R² and R³, which can be identical or different, each represent hydrogen, straight-chain or branched alkyl with 1 to 10 carbon atoms, cyanoethyl, 2-alkoxyethyl with 1 to 5 (especially 1 to 3) carbon atoms in the alkoxy group, allyl, propargyl, 1-methylpropargyl, 1,1-dimethylpropargyl, cyclopentyl, cyclohexyl, phenyl, nitrophenyl, tolyl, nitrotolyl, chlorophenyl, naphthyl, benzyl, chlorobenzyl, chlorotolyl, morpholinyl or the tetrahydrofurfuryl radical, or, together with the nitrogen atom to which they are bonded, represent pyrrolidyl, monoalkyl- or dialkyl-pyrrolidyl with 1 to 5 (especially 1 to 3) carbon atoms per alkyl group, morpholinyl, monoalkyl- or dialkylmorpholinyl with 1 to 5 (especially 1 to 3) carbon atoms per alkyl group, piperidyl, monoalkyl-, dialkyl- or trialkylpiperidyl with in each case 1 to 5 (especially 1 to 3) carbon atoms per alkyl group, spiro-substituted piperidyl (especially the radical of the formula

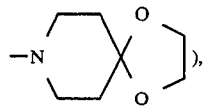

perhydro-azepinyl (=the hexamethyleneimino radical), 1,2,3,4-tetrahydroindolyl, monoalkyl-, dialkyl- or trialkyl-1,2,3,4-tetrahydroindolyl with in each case 1 to 5 (especially 1 to 3) carbon atoms per alkyl group, perhydroindolyl, monoalkyl-, dialkyl- or trialkyl-perhydroindolyl with in each case 1 to 5 (especially 1 to 3) carbon atoms per alkyl group, 1,2,3,4-tetrahydroquinolyl, 1,2,3,4-tetrahydroiso-quinolyl, monoalkyl-, dialkyl- or trialkyl-1,2,3,4-tetrahydroquinolyl or -isoquinolyl with in each case 1 to 5 (especially 1 to 3) carbon atoms per alkyl group, perhydroquinolyl, perhydroiso-quinolyl, monoalkyl, dialkyl- or trialkyl-perhydroquinolyl or -isoquinolyl with in each case 1 to 5 (especially 1 to 3) carbon atoms per alkyl group, perhydrothiazolyl or the radical of the formula

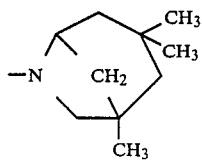

and

X represents oxygen or sulphur.

A sub-class of substituted carboxylic acid amides that is of interest is constituted by those compounds of the formula (I) in which n represents 1, R represents hydrogen, halogen, alkyl, halogenoalkyl, alkoxy, halogenoalkoxy, alkylthio, halogenoalkylthio, amino, alkylamino, dialkylamino, nitro, cyano or alkoxycarbonyl, R¹ represents hydrogen or alkyl, R² and R³ are identical or different and individually represent hydrogen, optionally substituted alkyl, alkenyl, alkynyl, aralkyl, cycloalkyl or aryl or, together with the nitrogen atom to which they are bonded, form an optionally substituted and optionally partially unsaturated monocyclic or bicyclic radical and X represents oxygen or sulphur.

The following compounds may be mentioned as specific examples of the carboxylic acid amides of the formula (I) according to the invention: benzthiazol-2-yloxy-acetic, benzoxazol-2-yloxy-acetic, α-(benzthiazol-2-yloxy)-propionic and benzoxazol-2-yloxy-propionic acid methylamide, ethylamide, n-propylamide, iso-propylamide, n-butylamide, iso-butylamide, dimethylamide, diethylamide, di-n-propylamide, di-iso-propyl-amide, N-methyl-N-iso-propylamide, N-methyl-N-iso-butylamide, N-methyl-N-sec.-butylamide, di-(2-ethyl-hexyl)-amide, N-methyl-N-(2-cyano-ethyl)-amide, di-(2-methoxy-ethyl)-amide, diallylamide, N-methyl-N-propargylamide, N-methyl-N-(1-methylpropargyl)-amide, dipropargylamide, cyclopentylamide, N-methyl-N-cyclopentylamide, cyclohexylamide, N-methyl-N-cyclohexylamide, anilide, 2-nitro-, 3-nitro- and 4-nitro-phenylamide, 2-chloro-, 3-chloro- and 4-chloro-phenylamide, 2,4-dichloro-, 2,5-dichloro-, 3,4-dichloro- and 3,5-dichloro-phenylamide, 2-methyl-, 3-methyl- and 4-methyl-phenylamide, N-methyl-anilide, N-methyl-N-(2-nitrophenyl)-, N-methyl-N-(3-nitrophenyl)- and N-methyl-N-(4-nitrophenyl)-amide, N-methyl-N-(2-chlorophenyl)-, N-methyl-N-(3-chlorophenyl)- and N-methyl-N-(4-chlorophenyl)-amide, N-methyl-N-(3-nitro-6-methyl-phenyl)-amide, N-ethyl-anilide, N-ethyl-N-(2-nitro-phenyl)-, N-ethyl-N-(3-nitro-phenyl)- and N-ethyl-N-(4-nitro-phenyl)-amide, N-ethyl-N-(2-chlorophenyl)-, N-ethyl-N-(3-chlorophenyl)- and N-ethyl-N-(4-chloro-phenyl)-amide, N-ethyl-N-(3-nitro-6-methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chlorophenyl)- and N-propyl-N-(4-chlorophenyl)-amide, N-propyl-N-(2-methyl-phenyl)-, N-propyl-N-(3-methyl-phenyl)- and N-propyl-N-(4-methyl-phenyl)-amide, N-propyl-N-(3-nitro-6-methyl-phenyl)-amide, N-butyl-anilide, N-butyl-N-(2-nitro-phenyl)-, N-butyl-N-(3-nitro-phenyl)- and N-butyl-N-(4-nitro-phenyl)-amide, N-butyl-N-(2-chloro-phenyl)-, N-butyl-N-(3-chloro-phenyl)- and N-butyl-N-(4-chloro-phenyl)-amide, N-butyl-N-(2-methyl-phenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl)- and N-iso-butyl-N-(4-nitro-phenyl)-amide, N-iso-butyl-N-(2-chloro-phenyl)-, N-iso-butyl-N-(3-chloro-phenyl)- and N-iso-butyl-N-(4-chloro-phenyl)-amide, N-iso-butyl-N-(2-methyl-phenyl)-, N-iso-butyl-N-(3-methyl-phenyl)- and N-iso-butyl-N-(4-methyl-phenyl)-amide, N-iso-butyl-N-(3-nitro-6-methyl-phenyl-amide, naphth-1-ylamide, naphth-2-ylamide, N-methyl-N-naphth-1-ylamide, N-methyl-N-naphth-2-ylamide, N-ethyl-N-naphth-1-ylamide, N-ethyl-N-naphth-2-ylamide, N-n-propyl-N-naphth-2-ylamide, N-iso-propyl-N-naphth-2-ylamide, N-n-butyl-N-naphth-2-ylamide, N-iso-butyl-N-naphth-2-ylamide, benzylamide, dibenzylamide, N-methyl-N-benzylamide, N-ethyl-N-benzylamide, N-propyl-N-benzylamide, N-butyl-N-benzyl-amide, pyrrolidide, 2-methyl-pyrrolidide, morpholide, piperidide, 2-methyl-piperidide, 4-methyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4,-tetrahydroindolide, 2-methyl-1,2,3,4-tetrahydroindolide, perhydroindolide, 2-methyl-perhydroindolide, 2,2,-dimethyl-perhydroindolide, 1,2,3,4-tetrahydroquinolide, 2-methyl-1,2,3,4-tetrahydroquinolide, perhydroquinolide, 2-methyl-perhydroquinolide, 1,2,3,4-tetrahydro-iso-quinolide and perhydroisoquinolide.

If hydroxyacetic acid piperidide and 2-bromo-benzthiazole are used as starting materials, the course of the reaction in the process according to the invention can be represented by the equation which follows:

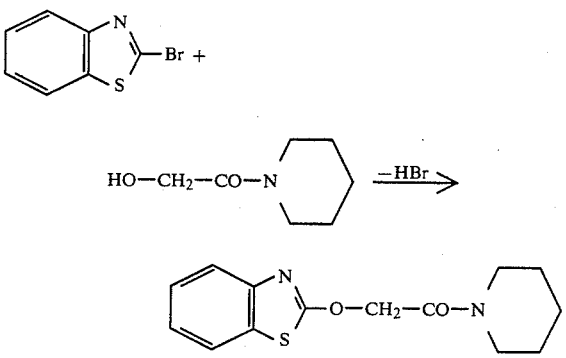

The formula (II) provides a general definition of the α-hydroxy-carboxylic acid amides to be used as starting substances. In this formula, $R^1$, $R^2$ and $R^3$ preferably represent those radicals which have already been mentioned as preferred in connection with the formula (I).

The following α-hydroxy-carboxylic acid amides may be mentioned as examples of starting materials of the formula (II): hydroxy-acetic and α-hydroxy-propionic acid methylamide, ethylamide, n-propylamide, iso-propylamide, n-butylamide, iso-butylamide, dimethylamide, diethylamide, di-n-propyl-amide, di-iso-propyl-amide, N-methyl-N-iso-propyl-amide, N-methyl-N-iso-butyl-amide, N-methyl-N-sec.-butyl-amide, di-(2-ethyl-hexyl)-amide, N-methyl-N-(2-cyano-ethyl)-amide, di-(2-methoxy-ethyl)-amide, diallyl-amide, N-methyl-N-propargyl-amide, N-methyl-N-(1-methyl-propargyl)-amide, dipropargyl-amide, cyclopentyl-amide, N-methyl-N-cyclopentyl-amide, cyclohexyl-amide, N-methyl-N-cyclohexyl-amide, anilide, 2-nitro-, 3-nitro- and 4-nitrophenyl-amide, 2-chloro-, 3-chloro- and 4-chloro-phenyl-amide, 2,4-dichloro-, 2,5-dichloro-, 3,4-dichloro and 3,5-dichlorophenyl-amide, 2-methyl-, 3-methyl- and 4-methyl-phenyl-amide, N-methyl-anilide, N-methyl-N-(2-nitro-phenyl)-, N-methyl-N-(3-nitro-phenyl)- and N-methyl-N-(4-nitro-phenyl)-amide, N-methyl-N-(2-chloro-phenyl)-, N-methyl-N-(3chloro-phenyl)- and N-methyl-N-(4-chloro-phenyl)-amide, N-methyl-N-(3-nitro-6-methyl-phenyl)-amide, N-ethyl-anilide, N-ethyl-N-(2-nitro-phenyl)-, N-ethyl-N-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chloro-phenyl)-amide, N-ethyl-N-(3-nitro-6-methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methyl-phenyl)- and N-propyl-N-( 4-methyl-phenyl)-amide, N-propyl-N-(3-nitro-6-methyl-phenyl)-amide, N-butyl-anilide, N-butyl-N-(2-nitro-phenyl)-, N-butyl-N-(3-nitro-phenyl)- and N-butyl-N-(4-nitro-phenyl)-amide, N-butyl-N-(2-chloro-phenyl)-, N-butyl-N-(3-chloro-phenyl)- and N-butyl-N-(4-chloro-phenyl)-amide, N-butyl-N-(2-methyl-phenyl)-, N-butyl-N-(3-methyl-phenyl)- and N-butyl-N-(4-methyl-phenyl)-amide, N-butyl-N-(3-nitro-6-methyl-phenyl)-amide, N-isobutyl-anilide, N-iso-butyl-N-(2-nitro-phenyl)-, N-iso-butyl-N-(3-nitro-phenyl)- and N-iso-butyl-N-(4-nitro-phenyl)-amide, N-iso-butyl-N-(2-chloro-phenyl)-, N-isobutyl-N-(3-chloro-phenyl)- and N-iso-butyl-N-(4-chloro-phenyl)-amide, N-iso-butyl-N-(2-methyl-phenyl)-, N-iso-butyl-N-(3-methyl-phenyl)- and N-iso-butyl-N-(4-methyl-phenyl)-amide, N-iso-butyl-N-(3-nitro-6-methyl-phenyl)-amide, naphth-1-ylamide, naphth-2-ylamide, N-methyl-N-naphth-1-ylamide, N-methyl-N-naphth-2-ylamide, N-ethyl-N-naphth-1-ylamide, N-ethyl-N-naphth-2-ylamide, N-n-propyl-N-naphth-2-ylamide, N-iso-propyl-N-naphth-2-ylamide, N-n-butyl-N-naphth-2-ylamide, N-iso-butyl-N-naphth-2-ylamide, benzylamide, dibenzylamide, N-methyl-N-benzylamide, N-ethyl-N-benzyl-amide, N-propyl-N-benzyl-amide, N-butyl-N-benzylamide, pyrrolidide, 2-methyl-pyrrolidide, morpholide, piperidide, 2-methyl-piperidide, 4-methyl-piperidide, 2,4-dimethyl-piperidide, 2,4,6-trimethyl-piperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6-ethyl-piperidide, 1,2,3,4-tetrahydroindolide, 2-methyl-1,2,3,4-tetrahydroindolide, perhydro-indolide, 2-methylperhydroindolide, 2,2-dimethyl-perhydro-indolide, 1,2,3,4-tetrahydroquinolide, 2-methyl-1,2,3,4-tetrahydroquinolide, perhydroquinolide, 2-methyl-perhydroquinolide, 1,2,3,4-tetrahydro-isoquinolide and perhydroisoquinolide.

Some of the α-hydroxy-carboxylic acid amides of the formula (II) are known (see DT-OS (German Published Specification) No. 2,647,481). They can be prepared from the corresponding α-hydroxy-carboxylic acids, as outlined in the equation below:

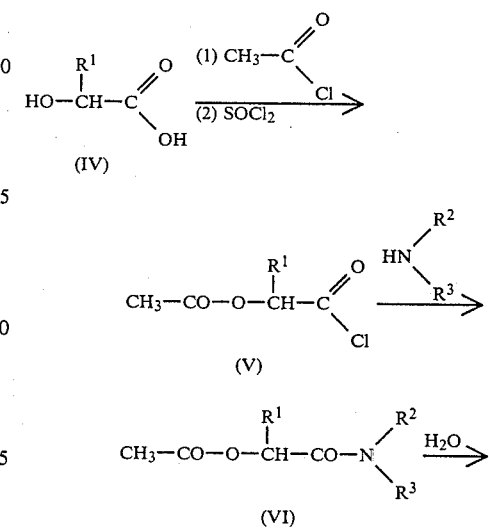

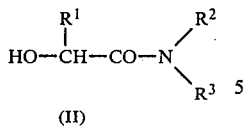

(II)

For this preparation, the α-hydroxy-carboxylic acids of the formula (IV), which are known from the literature, are first reacted with an acylating agent, for example acetyl chloride, at temperatures between 0° and 50° C., preferably between 20° and 30° C., and the resulting reaction mixtures are then treated with a chlorinating agent, for example thionyl chloride, at temperatures between 20° and 100° C., preferably between 40° and 90° C.

The products thus obtained of the formula (V), which are purified by distillation, can be converted into the acid amides of the formula (VI) in a conventional manner by reaction with the corresponding amines, if appropriate in the presence of an inert diluent, at temperatures between −10° and +50° C., preferably between 0° and +30° C. Working up and purification of these products are effected by customary methods, by washing the reaction mixtures with water, drying the organic phase, distilling off the solvent and if appropriate recrystallizing the residue. The compounds of the formula (VI) are deacylated to give the compounds of the formula (II) by reaction with aqueous-alcoholic sodium hydroxide solution at temperatures between 0° and 50° C., preferably between 10° and 40° C. In order to isolate and purify the products, the solvents are distilled off in vacuo, the residue is extracted with an organic solvent, for example methylene chloride, the solution is dried and the solvent is distilled off. Purification can be effected, for example, by recrystallization.

The formula (III) provides a definition of the 2-halogeno-benzazoles also to be used as starting materials. In this formula, R preferably represents those radicals which have already been mentioned as preferred in connection with the formula (I); Hal preferably represents chlorine or bromine, and n represents 1, 2, 3 or 4.

Examples of starting materials of the formula (III) which may be mentioned are: 2-chloro- and 2-bromo-benzthiazole and 2-chloro- and 2-bromo-benzoxazole.

The benzazoles of the formula (III) are known compounds (see Am. Chem. Journal 21, pages 111–167 (1899); J. Prakt. Chem [2] 42, pages 445–457 (1890); DT-OS (German Published Specification) No. 1,164,413 and British Patent Specification No. 913,910).

The process for the preparation of the carboxylic acid amides of the formula (I) according to the invention is preferably carried out using a suitable solvent or diluent. Possible solvents or diluents are virtually all the inert organic solvents, especially alcohols, such as methanol, ethanol and n- and iso-propanol; ethers, such as diethyl ether, dibutyl ether, tetrahydrofuran and dioxan; ketones, such as acetone, methyl ethyl ketone, methyl isopropyl ketone and methyl isobutyl ketone; nitriles, such as acetonitrile and propionitrile; and the highly polar solvents dimethylformamide, dimethylsulphoxide, sulpholane and hexamethylphosphoric acid triamide.

Any of the acid-binding agents which can customarily be used may be employed as acid acceptors in carrying out the process according to the invention. Preferred acid-binding agents include alkali metal hydroxides, such as sodium hydroxide and potassium hydroxide, alkali metal carbonates, such as sodium carbonate and bicarbonate and potassium carbonate and bicarbonate, alkali metal alcoholates, such as sodium methylate and ethylate and potassium methylate and ethylate, and aliphatic, aromatic or heterocyclic amines, for example triethylamine, di-methylaniline, dimethylbenzylamine, pyridine and diazabicyclooctane.

The reaction temperature can be varied within a substantial range. In general, the reaction is carried out between 0° and 80° C., preferably at from 10° to 50° C. It is generally carried out under normal pressure.

In carrying out the process according to the invention, 1.0 to 1.2 moles of a-hydroxy-carboxylic acid amide of the formula (II) and 1.0 to 1.5 molar equivalents of an acid acceptor are generally employed per mole of benzazole of the formula (III). In general, the reaction is carried out in a suitable diluent, and the reaction mixture is stirred at the required temperature for several hours.

Isolation of the products is effected by customary methods. In general, the reaction mixture is poured into water and neutralized with an acid, for example acetic acid, whereupon the reaction products are as a rule obtained in the crystalline form. The products are filtered off and purified, if appropriate, by recrystallization.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired. Whether the compounds according to the invention act as total herbicides or selective herbicides depends essentially on the amount used.

The active compounds according to the present invention may be used, for example, to combat the following plants:

dicotyledon weeds of the genera: Sirapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea; and monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera: Oryza, Zea, Triticum, Hordeum, Avena, Secale, Sorghum, Panicum, Saccharum, Ananas, Asparagus and Allium.

However the use of the active compounds according to the invention is in no way restricted to these genera, but also extends in the same manner to other plants.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good action against graminaceous weeds, the active compounds according to the invention also exhibit, in particular, a good herbicidal action in the case of broad-leaved weeds. It is possible to employ the active compounds according to the invention selectively, preferably for beet, soya beans, cotton, rice and other types of cereal.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with other herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably employed before emergence of the plants, that is to say by the pre-emergence process. They can also be incorporated into the soil before sowing.

The amount of active compound used can vary within a substantial range. It depends essentially on the nature of the desired effect. In general, the amounts used are from 0.1 to 10 kg of active compound per hectare, preferably from 0.1 to 5 kg/ha.

When used in certain concentrations, some of the active compounds according to the invention also display a fungicidal action, for example against the fungus *Pyricularia oryzae*, which is found, in particular, in rice crops.

The present invention also provides a herbicidal composition containing as active ingredient a compound of the present invention in admixture with a solid carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds or being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)

100% = total destruction

In this test, for example, the following compounds exhibited an excellent action: (1), (2), (16), (17), (20), (24), (30), (32), (35), (37), (48), (51), (77) and (78).

PREPARATIVE EXAMPLES

EXAMPLE 1

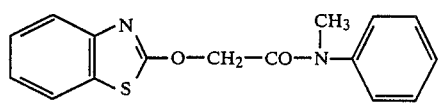 (1)

17 g (0.1 mol) of 2-chlorobenzthiazole were added to a solution of 7.5 g (0.13 mol) of potassium hydroxide powder and 18.9 g (0.11 mol) of hydroxyacetic acid N-methylanilide as 20° C. The mixture was stirred at 40° C. for two hours. For working up, the reaction mixture was poured into water and neutralized with acetic acid. After the product had crystallized, it was filtered off, washed once with water and once with ligroin and dried.

Yield: 25 g (84% of theory) of benzthiazol-2-yloxy-acetic acid N-methylanilide, white crystals of melting point: 118° C.

The following compounds of the general formula

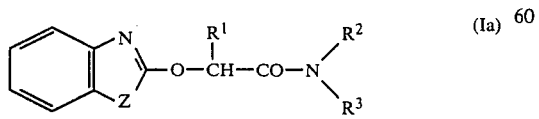 (Ia)

could be prepared analogously to Example 1 (refractive indices are $n_D^{20}$ determinations, unless otherwise stated; melting points are in °C.).

TABLE 1

| Example No. | $R^1$ | $-N\begin{matrix}R^2\\R^3\end{matrix}$ | X | Refractive index; melting point |
|---|---|---|---|---|
| 2 | H | piperidine with CH₃ substituent | S | 81 |
| 3 | H | $-N(C_2H_5)(2\text{-}ClC_6H_4)$ | S | 121 |
| 4 | H | morpholine | S | 155 |
| 5 | H | $-N(CH_2CH(CH_3)_2)(C_6H_5)$ | S | 93 |
| 6 | H | $-N(CH_2CH_2CH_2CH_3)(C_6H_5)$ | S | 79 |
| 7 | H | $-N(CH_2C_6H_5)_2$ | S | 114 |
| 8 | H | $-N(CH(CH_3)_2)_2$ | S | 94 |
| 9 | H | $-N(CH_3)(2\text{-}CH_3\text{-}4\text{-}NO_2\text{-}C_6H_3)$ wait see below | S | 155 |
| 10 | H | $-N(CH_3)-CH(CH_3)-CH_2CH_3$ | S | 1.5742 |
| 11 | H | $-N(CH_2CH_2OCH_3)_2$ | S | 1.5821 |
| 12 | H | $-N(C_2H_5)(1\text{-naphthyl})$ | S | 172 |
| 13 | H | $-N(CH_2-CH(C_2H_5)(CH_2)_3CH_3)$ | S | 1.5263 |

TABLE 1-continued

| Example No. | R¹ | −N(R²)(R³) | X | Refractive index; melting point |
|---|---|---|---|---|
| 14 | H | −N(CH₃)−CH₂−CH₂−CN | S | 90 |
| 15 | H | N-methyl-N-cyclohexyl (−N(CH₃)−C₆H₁₁) | S | 1.5495 |
| 16 | H | −N(CH₃)−CH(CH₃)−C≡CH | S | 106 |
| 17 | H | −N(CH₃)−(2-methylphenyl) | S | 124 |
| 18 | H | 1-(1-methylethyl)-naphthalen-2-yl amino | S | 161 |
| 19 | H | 1,2,3,4-tetrahydroisoquinolin-2-yl | S | 104 |
| 20 | H | 2,4-dimethylpiperidin-1-yl | S | 1.5800 |
| 21 | H | 2-methyl-2,3-dihydro-1H-indol-1-yl | S | 102 |
| 22 | H | decahydroquinolin-1-yl | S | 1.5422 |
| 23 | H | octahydro-1H-indol-1-yl | S | 93 |
| 24 | H | 1,2,3,4-tetrahydroquinolin-1-yl | S | 1.6363 |
| 25 | H | 2,4-dimethylpiperidin-1-yl (isomer) | S | 1.5370 |
| 26 | H | 4-ethyl-2-methylpiperidin-1-yl | S | 1.5651 |
| 27 | H | 6-methyl-decahydroquinolin-1-yl | S | 1.5776 |
| 28 | H | 2-methyl-decahydroquinolin-1-yl | S | 107 |
| 29 | H | 2,2-dimethyl-decahydroquinolin-1-yl | S | 1.5775 |
| 30 | H | −N(CH₃)−phenyl | O | 162 |
| 31 | H | morpholin-4-yl | O | 132 |

TABLE 1-continued
| Example No. | R¹ | -N(R²)(R³) | X | Refractive index; melting point |
|---|---|---|---|---|
| 32 | H |  | O | 140 |
| 33 | H | 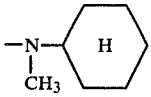 | O | 180 |
| 34 | H | —N(CH₃)—CH₂CH₂CN | O | 82 |
| 35 | H | 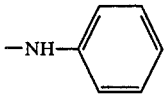 | O | 140 |
| 36 | H | 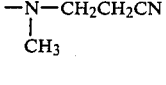 | O | 161–163 |
| 37 | H | —N(CH₂CH₂OCH₃)₂ | O | 88 |
| 38 | H | —N(CH₂—CH(C₂H₅)(CH₂)₃CH₃)₂ | O | 66 |
| 39 | CH₃ | 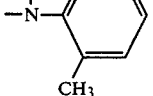 | O | 114–116 |
| 40 | H | 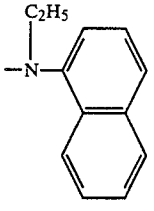 | S | 1.5766 (n$_D^{23}$) |
| 41 | H | —NHCH₃ | S | 135 |
| 42 | H | 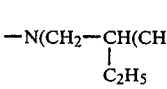 | S | 159 |
| 43 | H | —N(CH₃)₂ | S | 129 |
| 44 | H |  | S | 116 |
| 45 | H | —N(C₂H₅)₂ | S | 1.5860 |
| 46 | H | 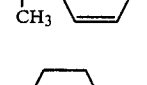 | S | 1.5860 |
| 47 | H | 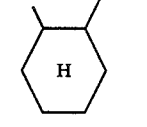 | S | 82 |
| 48 | H | —N(CH₂CH=CH₂)₂ | S | 1.5781 |
| 49 | H | 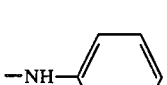 | S | 112 |
| 50 | H | 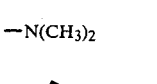 | S | n$_D^{23}$: 1.5766 |
| 51 | H | 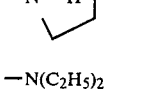 | S | n$_D^{22}$: 1.5730 |
| 52 | H |  | S | n$_D^{22.5}$: 1.5225 |
| 53 | H |  | S | n$_D^{21}$: 1.6173 |
| 54 | H | —NH—CH(CH₃)—CH₂—CH₃ | S | 1.5773 |
| 55 | H | —N(CH₂—CH(CH₃)—CH₃)₂ | S | 58 |
| 56 | H | —NH—C(CH₃)₂—C≡CH | S | 116 |
| 57 | H |  | S | 202 |

TABLE 1-continued

| Example No. | R¹ | -N(R²)(R³) | X | Refractive index; melting point |
|---|---|---|---|---|
| 58 | H | -NH-CH₂-(tetrahydrofuran-2-yl) | S | 90 |
| 59 | H | -N(CH₂CH₂SCH₂) (thiazolidine ring) | S | 130 |
| 60 | H | -NH-CH₂-CH(CH₃)-CH₃ | S | 1.5699 |
| 61 | H | -N(CH₃)-CH₂-C≡CH | S | 108 |
| 62 | CH₃ | -N(CH₂-CH=CH₂)₂ | S | 100 |
| 63 | H | -N(phenyl)(CH₂-CH=CH₂) | S | 111 |
| 64 | H | -N(cyclohexyl)(CH₂-CH=CH₂) | S | 78 |
| 65 | H | 2,6-dimethylmorpholino | S | 164 |
| 66 | H | -NH-CH(CH₃)-phenyl | S | 65 |
| 67 | H | -NH-CH₂CH₂-phenyl | S | 141 |
| 68 | H | -N(phenyl)(CH₂-phenyl) | S | 118 |
| 69 | CH₃ | -N(CH₂-CH(CH₃)-CH₃)₂ | S | $n_D^{21}$: 1.5238 |
| 70 | H | 3,3,5-trimethyl-piperidine (with CH₂-CH₃ bridge) | S | 139 |
| 71 | H | octahydroazocine (N-containing 8-membered ring) | S | 110 |
| 72 | H | 2-methylindoline | S | 122 |
| 73 | H | 1,4-dioxa-8-azaspiro[4.5]decane | S | 124 |
| 74 | H | 3,3,6-trimethyl-hexahydroazepine | S | 103 |
| 75 | H | -N(CH₂)₁₂ (azacyclotridecane) | S | 90 |
| 76 | H | -N(CH₂-phenyl)(CH₂-C≡CH) | S | 90 |
| 77 | H | -N(H)-CH(CH₃)(CH(CH₃)-CH₂CH₃)  — -N-CH(CH₃CH₃)-CH₂CH₃ | O | 1.5983 |
| 78 | H | -N(H)-CH(CH₃CH₃)-C≡CH | O | 93 |
| 79 | H | -N(phenyl)-CH₂-CH(CH₃)-CH₃ | O | $n_D^{21}$: 1.5616 |

TABLE 1-continued

| Example No. | R¹ | -N(R²)(R³) | X | Refractive index; melting point |
|---|---|---|---|---|
| 80 | H | -N(CH₂CH₂CH₂CH₃)(phenyl) | O | 87 |
| 81 | H | 1,2,3,4-tetrahydroisoquinolin-2-yl | O | 110 |
| 82 | H | -N(CH₂CH=CH₂)₂ | O | $n_D^{21}$: 1.5495 |
| 83 | H | 2,6-dimethylmorpholin-4-yl | O | 118 |
| 84 | H | 4-ethyl-2-methylpiperidin-1-yl (NH) | O | $n_D^{21}$: 1.5425 |
| 85 | H | 3,3,5,5-tetramethyl (bicyclic amine) | O | 142 |
| 86 | H | hexamethyleneimino (azepan-1-yl, NH) | O | 100 |
| 87 | H | thiazolidin-3-yl (NH) | O | 94–96 |
| 88 | H | -N(CH₃)-CH₂-C≡CH | O | 80–82 |
| 89 | H | -NH-C(CH₃)₂-C≡CH | O | 111 |
| 90 | H | -NH-CH₂-CH(CH₃)-CH₃ | O | 83 |
| 91 | H | -NH-CH₂-(tetrahydrofuran-2-yl) | O | 1.5758 |
| 92 | H | -N(CH₂CH(CH₃)CH₃)₂ | O | 93 |
| 93 | H | 2-methylpiperidin-1-yl (NH) | O | $n_D^{24}$: 1.5560 |
| 94 | H | -NH-CH(CH₃)CH₂CH₃ | O | $n_D^{24}$: 1.5735 |
| 95 | H | 2-methyl-1,2,3,4-tetrahydroquinolin-1-yl (NH) | O | 122 |
| 96 | H | 3,3,5-trimethylazepan-1-yl (NH) | O | 109 |
| 97 | H | 2-ethylpiperidin-1-yl (NH) | O | $n_D^{21}$: 1.5440 |
| 98 | H | -N⟨(CH₂)₁₂⟩ | O | 148 |
| 99 | H | -N(CH₂-phenyl)(CH₂-C≡CH) | O | 83 |

The following compounds of the formula (I)

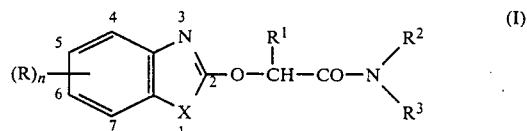

could also be prepared analogously to Example 1.

TABLE 2

| Example No. | n | R | R¹ | -N(R²)(R³) | X | Refractive index; melting point (°C.) |
|---|---|---|---|---|---|---|
| 100 | 2 | 4,6-Cl | H | -N(CH₃)-C₆H₅ | O | 116 |
| 101 | 1 | 6-CF₃ | H | -N(CH₃)-C₆H₅ | S | 126 |
| 102 | 1 | 5-OCF₃ | H | -N(CH₃)-C₆H₅ | S | 84 |
| 103 | 2 | F₂C(O-(4))(O-(5)) | H | 2-methylpiperidin-1-yl | S | 93 |
| 104 | 1 | 6-OC₂H₅ | H | -N(CH₃)-C₆H₁₁ | S | 124–132 |
| 105 | 1 | 6-OC₂H₅ | H | -N(CH₃)-CH(CH₃)-C≡CH | S | 129 |
| 106 | 1 | 6-OC₂H₅ | H | -N(CH₃)-C₆H₅ | S | 137–139 |
| 107 | 1 | 6-OC₂H₅ | H | -N(CH₂CH₂OCH₃)₂ | S | $n_D^{21}$: 1.5623 |
| 108 | 3 | 4,6,7-Cl | H | -N(CH₃)-C₆H₅ | S | 183 |
| 109 | 2 | 4,6-F | H | -N(CH₃)-C₆H₅ | S | 88 |
| 110 | 4 | H | H | -NH-(CH₂)₁₇-CH₃ | S | |
| 111 | 4 | H | H | -NH-CH₂CH₂-OCH₃ | S | |
| 112 | 4 | H | H | -N(C₂H₅)-CH(CH₃)-CH₃ | S | |
| 113 | 4 | H | H | 4-ethylpiperidin-1-yl | S | |
| 114 | 1 | 5-Cl | H | 3-ethylpiperidin-1-yl | O | |

TABLE 2-continued
| Example No. | n | R | R¹ | -N(R²)(R₃) | X | Refractive index; melting point (°C.) |
|---|---|---|---|---|---|---|
| 115 | 1 | 5-Cl | H | 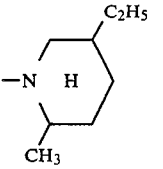 | O | |
| 116 | 1 | 5-Cl | H | 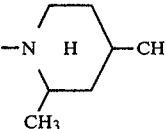 | O | |
| 117 | 1 | 5-Cl | H | 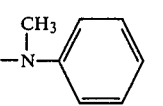 | O | |
| 118 | 1 | 6-OC₂H₅ | H | 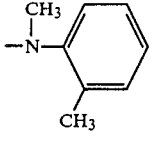 | S | |
| 119 | 1 | 6-OC₂H₅ | H | 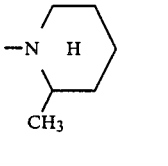 | S | |
| 120 | 4 | H | H | 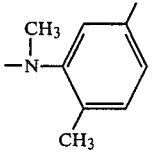 | O | |
| 121 | 4 | H | H | —N(C₂H₅)₂ | O | |
| 122 | 4 | H | H | 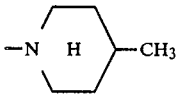 | O | |
| 123 | 4 | H | H | —N(CH₃)₂ | O | |
| 124 | 4 | H | H | 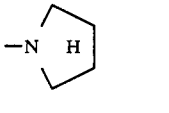 | O | |
| 125 | 4 | H | H | 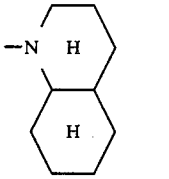 | O | |

TABLE 2-continued

| Example No. | n | R | R¹ | $-N{<}^{R^2}_{R_3}$ | Refractive index; melting point (°C.) X |
|---|---|---|---|---|---|
| 126 | 4 | H | H | 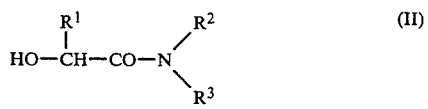 | O |

The α-hydroxy-carboxylic acid amides of the general formula

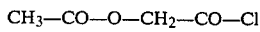

$$HO-CH(R^1)-CO-N{<}^{R^2}_{R^3} \quad (II)$$

to be used as starting compounds could be prepared, for example, as follows:

(a)

$$CH_3-CO-O-CH_2-CO-Cl$$

141 g (1.7 mol) of acetyl chloride were added dropwise to 76 g (1 mol) of anhydrous hydroxyacetic acid at 20° to 30° C., whereupon vigorous evolution of hydrogen chloride could be observed. The mixture was heated to a temperature of 90° to 100° C. for 3 hours; excess acetyl chloride was then distilled off. The residue was warmed to 30° C. and 174 g (1.42 mol) of thionyl chloride were added dropwise thereto. The reaction mixture was heated to the boil for 3 hours. Working up was effected by vacuum distillation.

Yield: 96 g (70% of theory) of acetoxyacetylchloride, a colorless liquid of boiling point: 65° C./30 mbars.

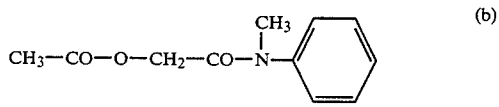

(b)

230 g (1.6 mol) of acetoxyacetyl chloride were added to 377 g (3.5 mol) of N-methylaniline in 800 ml of toluene at 0° to 10° C. and the mixture was stirred at 20° C. for about 15 hours. For working up, the mixture was poured into water and the organic phase was washed with dilute hydrochloric acid and then with water, dried and concentrated. The product thereby crystallized out.

Yield: 246 g (74% of theory) of acetoxy-N-methylacetanilide, yellowish crystals of melting point: 91° C.

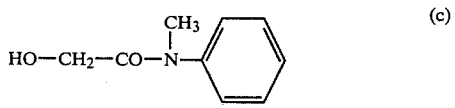

(c)

197 ml (2.38 mol) of concentrated sodium hydroxide solution were added to 432 g (2.16 mol) of acetoxy-N-methylacetanilide in 1082 ml of methanol at 30° C. and the mixture was stirred at 20° C. for 15 hours. It was then concentrated at 40° C. in vacuo and the residue was extracted with methylene chloride. The methylene chloride solution was freed from undissolved sodium acetate by filtration and the filtrate was dried with sodium sulphate. On concentrating, the product crystallized out.

Yield: 308 g (86% of theory) of hydroxyacetic acid N-methylanilide, pale yellow crystals of melting point: 45° C.

It will be understood that the specification and examples are illustrative but not limitative of the present invention and that other embodiments within the spirit and scope of the invention will suggest themselves to those skilled in the art.

What is claimed is:

1. Substituted carboxylic acid amide compound of the formula

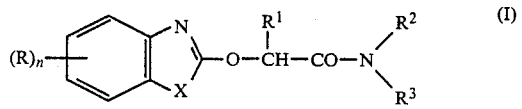

wherein
n is 1 or 2;
each R is independently selected from hydrogen, halogen, trifluoromethyl, alkoxy with 1 to 2 carbon atoms, and trifluoromethoxy, and two R substituents taken together can form difluoromethylenedioxy;
R¹ is hydrogen;
R² and R³ are individually selected from alkyl with 1 to 18 carbon atoms, allyl, alkynyl with 3 to 5 carbon atoms, phenylalkyl with 1 to 2 carbon atoms in the alkyl part, cyanoethyl, alkoxyalkyl with 2 to 3 carbon atoms, cyclohexyl, and aryl with 6 or 10 carbon atoms, or R² and R³ together with the nitrogen atom to which they are bonded, form a pyrrolidinyl, piperidinyl, perhydroazepinyl or dodecamethyleneimino radical, which is optionally substituted by 1 to 3 alkyl groups with 1 to 2 carbon atoms per alkyl group; and
X is sulfur.

2. Substituted carboxylic acid amide compound as claimed in claim 1 wherein n is 1.

3. Substituted carboxylic acid amide compound as claimed in claim 1 wherein n is 2.

4. Substituted carboxylic acid amide compound as claimed in claim 1 wherein R is hydrogen.

5. Substituted carboxylic acid amide compound as claimed in claim 1 wherein R is halogen.

6. Substituted carboxylic acid amide compound as claimed in claim 1 wherein R is trifluoromethyl.

7. Substituted carboxylic acid amide compound as claimed in claim 1 wherein R is alkoxy with 1 to 2 carbon atoms.

8. Substituted carboxylic acid amide compound as claimed in claim 1 wherein R is trifluoromethoxy.

9. Substituted carboxylic acid amide compound as claimed in claim 1 wherein at least one of $R^2$ and $R^3$ is alkyl of up to 18 carbon atoms.

10. Substituted carboxylic acid amide compound as claimed in claim 1 wherein at least one of $R^2$ and $R^3$ is cyanoethyl.

11. Substituted carboxylic acid amide compound as claimed in claim 1 wherein at least one of $R^2$ and $R^3$ is alkoxyalkyl of 2 to 8 carbon atoms.

12. Substituted carboxylic acid amide compound as claimed in claim 1 wherein at least one of $R^2$ and $R^3$ is alkynyl of 3 to 5 carbon atoms.

13. Substituted carboxylic acid amide compound as claimed in claim 1 wherein at least one of $R^2$ and $R^3$ is cyclohexyl.

14. Substituted carboxylic acid amide compound as claimed in claim 1 wherein at least one of $R^2$ and $R^3$ is phenylalkyl with 1 or 2 carbon atoms in the alkyl moiety.

15. Substituted carboxylic acid amide compound as claimed in claim 1 wherein at least one of $R^2$ and $R^3$ is aryl of 6 or 10 carbon atoms.

16. Substituted carboxylic acid amide compound as claimed in claim 1 wherein $R^2$ and $R^3$ are individually straight-chain or branched alkyl with 1 to 10 carbon atoms, cyanoethyl, 2-alkoxyethyl with 1 to 5 carbon atoms in the alkoxy group, allyl, propargyl, 1-methyl-propargyl, 1,1-dimethyl-propargyl, cycolopentyl, cyclohexyl, phenyl, nitrophenyl, tolyl, nitrotolyl, chlorophenyl, napthyl, benzyl, chlorobenzyl, chlorotolyl, or, together with the nitrogen atom to which they are bonded, represent pyrrolidyl, monoalkyl- or dialkyl-pyrrolidyl with 1 to 5 carbon atoms per alkyl group.

17. Substituted carboxylic acid amide compound as claimed in claim 1 wherein said compound is benzthiazol-2-yloxy-acetic acid N-methylanilide.

18. Substituted carboxylic acid amide compound as claimed in claim 1 wherein said compound is benzthiazol-2-yloxy-acetic acid 2-methyl-pyrrolidide.

19. Substituted carboxylic acid amide compound as claimed in claim 1 wherein said compound is benzthiazol-2-yloxy-acetic acid N-methyl-2-methyl-5-nitro-anilide.

20. Substituted carboxylic acid amide compound as claimed in claim 1 wherein said compound is benzthiazol-2-yloxy-acetic acid 2,4-dimethyl-pyrrolidide.

21. Substituted carboxylic acid amide compound as claimed in claim 1 wherein said compound is benzthiazol-2-yloxy-acetic acid N-methyl-N-(1-methyl-propargyl)-amide.

22. Herbicidal composition comprising an agriculturally acceptable carrier and in herbicidally effective amounts a substituted carboxylic acid amide compound as claimed in claim 1.

23. Method of combating weeds which method comprises applying to such weeds or their habitat a herbicidally effective amount of a substituted carboxylic acid amide compound as claimed in claim 1.

24. Method as claimed in claim 23 wherein said compound is selected from benzthiazol-2-yloxy-acetic acid N-methylanilide, benzthiazol-2-yloxy-acetic acid 2-methyl-pyrrolidide, benzthiazol-2-yloxy-acetic acid N-methyl-2-methyl-5-nitro-anilide, benzthiazol-2-yloxy-acetic acid 2,4-dimethyl-pyrrolidide and benzthiazol-2-yloxy-acetic acid N-methyl)-N-(1-methyl-propargyl)-amide.

25. A method as claimed in claim 23 wherein the compound is applied at a dosage of 0.1 to 10 kg per hectare.

26. A method as claimed in claim 25 wherein the compound is applied at a dosage of 0.1 to 5 kg per hectare.

27. Method of combating weeds which method comprises applying to such weeds or their habitat a herbicidally effective amount of benzthiazol-2-yloxy-acetic acid N-methylanilide.

* * * * *

UNITED STATES PATENT AND TRADEMARK OFFICE
CERTIFICATE OF CORRECTION

PATENT NO. : 4,509,971

DATED : April 9, 1985

INVENTOR(S) : Heinz Förster, et al.

It is certified that error appears in the above-identified patent and that said Letters Patent is hereby corrected as shown below:

Column 1, line 30 "now" should be -- not --.

Column 8, line 41 "Sirapis" should be -- Sinapis --.

Column 11, line 64, "Z" should be -- X --.

Column 13, line 61, "93" should be -- 95 --.

Claim 24, line 7 delete ")".

Signed and Sealed this

Twelfth Day of November 1985

[SEAL]

Attest:

Attesting Officer

DONALD J. QUIGG

Commissioner of Patents and Trademarks